(12) United States Patent
Siegel et al.

(10) Patent No.: US 9,050,448 B2
(45) Date of Patent: Jun. 9, 2015

(54) ULTRASONIC BATH TO INCREASE TISSUE PERFUSION

(75) Inventors: Robert J. Siegel, Beverly Hills, CA (US); Yochai Birnbaum, Houston, TX (US); Huai Luo, Los Angeles, CA (US)

(73) Assignees: Cedars-Sinai Medical Center, Los Angeles, CA (US); Board of Regents of the University of Texas System, Austin, TX (US)

( * ) Notice: Subject to any disclaimer, the term of this patent is extended or adjusted under 35 U.S.C. 154(b) by 1036 days.

(21) Appl. No.: 12/520,041

(22) PCT Filed: Dec. 19, 2007

(86) PCT No.: PCT/US2007/088118
§ 371 (c)(1),
(2), (4) Date: Jun. 18, 2009

(87) PCT Pub. No.: WO2008/077096
PCT Pub. Date: Jun. 26, 2008

(65) Prior Publication Data
US 2010/0063423 A1    Mar. 11, 2010

Related U.S. Application Data

(60) Provisional application No. 60/870,701, filed on Dec. 19, 2006.

(51) Int. Cl.
*A61H 33/00* (2006.01)
*A61N 7/00* (2006.01)
*A61H 35/00* (2006.01)

(52) U.S. Cl.
CPC *A61N 7/00* (2013.01); *A61H 33/00* (2013.01); *A61H 35/00* (2013.01)

(58) Field of Classification Search
None
See application file for complete search history.

(56) References Cited

U.S. PATENT DOCUMENTS

| | | | | | |
|---|---|---|---|---|---|
| 2,970,073 | A | * | 1/1961 | Prange | 134/1 |
| 3,023,611 | A | * | 3/1962 | Howry | 73/621 |
| 3,499,436 | A | * | 3/1970 | Balamuth | 601/2 |
| 3,550,586 | A | * | 12/1970 | Balamuth | 601/2 |
| 3,765,403 | A | * | 10/1973 | Brenden | 600/448 |
| 3,867,929 | A | * | 2/1975 | Joyner et al. | 601/166 |
| 4,216,766 | A | * | 8/1980 | Duykers et al. | 600/586 |
| 4,780,212 | A | * | 10/1988 | Kost et al. | 210/646 |
| 4,786,277 | A | * | 11/1988 | Powers et al. | 604/20 |
| 4,787,394 | A | * | 11/1988 | Ogura | 600/439 |
| 4,905,671 | A | * | 3/1990 | Senge et al. | 601/4 |
| 4,942,868 | A | * | 7/1990 | Vago | 601/2 |
| 4,945,901 | A | * | 8/1990 | Burcke, Jr. | 601/157 |
| 5,048,520 | A | * | 9/1991 | Vago | 601/2 |
| 5,086,788 | A | * | 2/1992 | Castel et al. | 607/150 |
| 5,149,319 | A | * | 9/1992 | Unger | 604/22 |
| 5,178,134 | A | * | 1/1993 | Vago | 601/2 |
| 5,318,035 | A | * | 6/1994 | Konno et al. | 600/459 |
| 5,339,804 | A | * | 8/1994 | Kemp | 601/2 |

(Continued)

*Primary Examiner* — Nicholas Evoy
(74) *Attorney, Agent, or Firm* — Seth D. Levy; Linda B. Huber; Nixon Peabody LLP (57) ABSTRACT

The present invention describes a method of using an ultrasonic bath to enhance tissue perfusion, enhance the development of collateral blood vessels and/or enhance collateral circulation in an extremity in need thereof. Also described is an ultrasonic bath adapted to hold media and to permit the immersion of an extremity and comprising one or more ultrasonic transducers to generate and transmit ultrasonic energy to the extremity or the inventive method.

12 Claims, 3 Drawing Sheets

(56) References Cited

U.S. PATENT DOCUMENTS

| | | | |
|---|---|---|---|
| 5,413,550 A * | 5/1995 | Castel | 601/2 |
| 5,524,620 A * | 6/1996 | Rosenschein | 600/407 |
| 5,595,178 A * | 1/1997 | Voss et al. | 600/427 |
| 5,665,141 A * | 9/1997 | Vago | 95/30 |
| 5,692,509 A * | 12/1997 | Voss et al. | 600/407 |
| 5,693,004 A * | 12/1997 | Carlson et al. | 601/23 |
| 5,904,659 A * | 5/1999 | Duarte et al. | 601/2 |
| 6,047,246 A * | 4/2000 | Vickers et al. | 702/105 |
| 6,190,336 B1 * | 2/2001 | Duarte et al. | 601/2 |
| 6,206,843 B1 * | 3/2001 | Iger et al. | 601/2 |
| 6,273,864 B1 * | 8/2001 | Duarte et al. | 601/2 |
| 6,390,995 B1 * | 5/2002 | Ogden et al. | 601/2 |
| 6,398,753 B2 * | 6/2002 | McDaniel | 604/22 |
| 6,436,060 B1 * | 8/2002 | Talish | 601/2 |
| 6,450,979 B1 * | 9/2002 | Miwa et al. | 601/2 |
| 6,478,754 B1 * | 11/2002 | Babaev | 601/2 |
| 6,569,099 B1 * | 5/2003 | Babaev | 600/439 |
| 6,576,220 B2 * | 6/2003 | Unger | 424/9.32 |
| 6,663,554 B2 * | 12/2003 | Babaev | 600/2 |
| 6,733,450 B1 * | 5/2004 | Alexandrov et al. | 600/439 |
| 6,964,647 B1 * | 11/2005 | Babaev | 604/22 |
| 7,090,974 B2 * | 8/2006 | Chu | 435/134 |
| 7,094,211 B2 * | 8/2006 | Krompasick | 601/90 |
| 7,108,663 B2 * | 9/2006 | Talish et al. | 601/2 |
| 7,393,323 B2 * | 7/2008 | Vago | 600/437 |
| 7,416,535 B1 * | 8/2008 | Kenny | 601/2 |
| 7,767,434 B2 * | 8/2010 | Chu | 435/286.1 |
| 7,837,719 B2 * | 11/2010 | Brogan et al. | 607/86 |
| 8,241,258 B2 * | 8/2012 | Pelkus | 604/289 |
| 8,353,853 B1 * | 1/2013 | Kyle et al. | 601/2 |
| 8,361,001 B2 * | 1/2013 | Filtvedt et al. | 601/151 |
| 8,603,014 B2 * | 12/2013 | Alleman et al. | 601/2 |
| 8,870,796 B2 * | 10/2014 | Hoffmann | 601/47 |
| 2002/0115960 A1 * | 8/2002 | Redding, Jr. | 604/22 |
| 2002/0156400 A1 * | 10/2002 | Babaev | 601/2 |
| 2002/0190136 A1 * | 12/2002 | Babaev | 239/102.2 |
| 2003/0083597 A1 * | 5/2003 | Vitek et al. | 601/2 |
| 2003/0199765 A1 * | 10/2003 | Stetten et al. | 600/439 |
| 2004/0024348 A1 * | 2/2004 | Redding, Jr. | 604/22 |
| 2004/0087883 A1 | 5/2004 | Berger | |
| 2004/0124746 A1 * | 7/2004 | Suzuki et al. | 310/326 |
| 2004/0131645 A1 * | 7/2004 | Williams et al. | 424/400 |
| 2005/0075587 A1 * | 4/2005 | Vago | 601/2 |
| 2005/0234439 A1 * | 10/2005 | Underwood | 606/32 |
| 2006/0094988 A1 * | 5/2006 | Tosaya et al. | 601/2 |
| 2006/0184074 A1 * | 8/2006 | Vaezy et al. | 601/2 |
| 2007/0039389 A1 * | 2/2007 | Brooks et al. | 73/579 |
| 2007/0167880 A1 * | 7/2007 | Vago | 601/2 |
| 2007/0167882 A1 * | 7/2007 | Guzzini | 601/3 |
| 2008/0319356 A1 * | 12/2008 | Cain et al. | 601/2 |
| 2009/0221902 A1 * | 9/2009 | Myhr | 600/411 |
| 2010/0022941 A1 * | 1/2010 | Pelkus | 604/20 |
| 2010/0063423 A1 * | 3/2010 | Siegel et al. | 601/2 |

\* cited by examiner

ULTRASONIC BATH TO INCREASE TISSUE PERFUSION

This application is the National Phase of International Application PCT/US07/188118, filed Dec. 19, 2007, which designated the U.S. and that International Application was published under PCT Article 21(2) in English. This application also includes a claim of priority under 35 U.S.C. §119(e) to U.S. provisional patent application No. 60/870,701, filed Dec. 19, 2006.

FIELD OF INVENTION

This invention relates to a method for using an ultrasonic bath to apply therapeutic ultrasonic energy to enhance tissue perfusion and collateral circulation and an apparatus for the same.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Peripheral Vascular Disease ("PVD"), also referred to as Peripheral Arterial Disease ("PAD"), is a general term for diseases caused by occlusion or obstruction of peripheral arteries. PVD is a common disease affecting numerous patients that may lead to morbidity and suffering. The occlusion of peripheral arteries via the processes of atherosclerosis, inflammatory response, embolism, thrombus formation and diabetes mellitus may all result in PVD. PVD may cause acute or chronic ischemia in the surrounding tissues, particularly in an extremity of the affected person. The acute or chronic ischemia may result in pain in the extremity (e.g., claudication), loss of sensation in the extremity, sores, wounds or ulcers that heal slowly or not at all, and tissue loss in the affected extremity. Ischemia is characterized by an absolute or relative shortage of blood supply to a tissue as a result of constricted or blocked blood vessels supplying the tissue.

The technology available to treat ischemia in an extremity includes invasive surgical arterial bypass operations, peripheral arterial balloon angioplasty and stent placement. However, in many patients and especially in those with diabetes mellitus, the occlusive disease affects small blood vessels that are not amenable to mechanical revascularization. Current technology tends to have limited long term success with high recurrence rates. Medical therapy is also available; however, the benefit is limited. The most severe cases require amputation of the extremity.

Thus, there is a need in the art for a method and a device for non-invasive treatment of ischemia and/or PVD. Further, there is a need for technology to enhance perfusion to the extremities, to enhance a body's ability to develop collateral blood vessels and to enhance collateral circulation.

SUMMARY OF THE INVENTION

The following embodiments and aspects thereof are described and illustrated in conjunction with compositions and methods which are meant to be exemplary and illustrative, not limiting in scope.

The present invention describes a method for enhancing tissue perfusion, enhancing development of collateral blood vessels and/or enhancing collateral circulation in an extremity in need thereof, comprising: providing an ultrasonic bath; placing a subject's extremity in need of treatment in the ultrasonic bath; and using the ultrasonic bath to apply ultrasonic energy to enhance tissue perfusion, develop collateral blood vessels and/or enhance collateral circulation. The method may further comprise applying heat to the extremity. In various embodiments, the extremity in need of treatment may be selected from the group consisting of an arm, hand, finger, leg, foot, toe and combinations thereof.

The ultrasonic bath used by the method may comprise: a basin adapted to hold media and to permit the immersion of an extremity; and one or more ultrasonic transducers to generate and transmit ultrasonic energy to the subject's extremity. In one embodiment, the basin may be about 20 inches in length, about 12 inches in width and about 40 inches in depth. In one embodiment, the ultrasonic bath may further comprise an inlet, an outlet or both. In another embodiment, the ultrasonic bath may further comprise a heating element. In another embodiment, the ultrasonic bath may further comprise an ultrasonic transducer control unit.

In various embodiments, the ultrasonic energy applied to the extremity may be at a frequency of about 18 kHz to about 3 mHz. In particular embodiments, the ultrasonic energy applied to the extremity may be at a frequency of about 19 kHz to about 40 kHz. In other embodiments, the ultrasonic energy may be at a power level of about 0.01 watt per $cm^2$ to about 20.0 watts per $cm^2$. In particular embodiments, the ultrasonic energy may be at a power level of about 0.25 watt per $cm^2$ to about 5.0 watts per $cm^2$. In one particular embodiment, the energy may be at a power level of about 1 watt per $cm^2$.

In one embodiment, using the ultrasonic bath may comprise applying ultrasonic energy for at least five minutes. In another embodiment, using the ultrasonic bath may comprise applying the ultrasonic energy for up to 90 minutes. In another embodiment, using the ultrasonic bath may comprise serial treatments for the extremity.

In another embodiment, the method may further comprise applying heat to the extremity.

The present invention also describes an ultrasonic bath for enhancing tissue perfusion, enhancing development of collateral blood vessels and/or enhancing collateral circulation in an extremity in need thereof, comprising: a basin adapted to hold media and to permit the immersion of an extremity; and one or more ultrasonic transducers to generate and transmit ultrasonic energy to the subject's extremity. The basin may be about 20 inches in length, about 12 inches in width and about 40 inches in depth. In various embodiments, the one or more ultrasonic transducers may be configured to generate and transmit ultrasonic energy at a frequency of about 18 kHz to about 3 mHz. In particular embodiments, the one or more ultrasonic transducers may be configured to generate and transmit ultrasonic energy at a frequency of about 19 kHz to about 40 kHz. The one or more ultrasonic transducers may be configured to generate and transmit the ultrasonic energy at a power level of about 0.01 watt per $cm^2$ to about 20.0 watts per $cm^2$. In particular embodiments, the one or more ultrasonic transducers may be configured to generate and transmit the ultrasonic energy at a power level of about 0.25 watt per $cm^2$ to about 5.0 watts per $cm^2$. In one particular embodiment, the one or more ultrasonic transducers may be configured to generate and transmit the ultrasonic energy at a power level of about 1.0 watts per $cm^2$.

The ultrasonic bath may further comprise an inlet, an outlet or both. In another embodiment, the ultrasonic bath may further comprise a heating element. In another embodiment, the ultrasonic bath may further comprise an ultrasonic transducer control unit.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); and March, *Advanced Organic Chemistry Reactions, Mechanisms and Structure* 5$^{th}$ ed., J. Wiley & Sons (New York, N.Y. 2001).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Extremity" as used herein refers to a limb of the body. Examples include but are not limited to arms, hands, fingers, legs, feet and toes.

"Extremity in need of treatment" as used herein refers to an extremity that is in need of treatment to enhance tissue perfusion, to enhance a body's ability to develop collateral blood vessels and/or to enhance collateral circulation.

"Media" as used herein refers to liquid, semi-solid (e.g., gel), or solid (e.g., small beads) substances capable of transferring ultrasonic energy from an ultrasonic transducer to an extremity and that will surround the extremity. Examples of media include but are not limited to water, including salt water, sterile water, and deoxygenated water. In embodiments wherein salt water is used, the concentration of salt may be any appropriate concentration; for example, about 0.25% to about 10%.

Embodiments of the present invention provide for methods and apparatuses for using ultrasonic energy to enhance collateral circulation and thereby enhance tissue perfusion.

The inventors have shown herein that ultrasound exposure through a water bath to an extremity increases tissue perfusion in the tissue of the extremity. The increase in tissue perfusion was found to be independent of a temperature increase in the water bath. While not wishing to be bound by any particular theory, the inventors believe that the enhanced tissue perfusion is due, in part, to mechanical vibration. Furthermore, the inventors have previously shown that ultrasound increases the expression and activity of endothelial nitric oxide synthase ("eNOS") and inducible nitric oxide synthanse ("iNOS"). (See Atar et al., "Low-frequency ultrasound increases activity and tissue content of nitric oxide synthase in acute limb ischemia in rabbits." *World Congress of Cardiology* 2006, Barcelona Spain. P 595.) The increased expression of these enzymes, particularly eNOS, corresponds to an increase in the release of nitric oxide, also known as endothelium derived relaxing factor ("EDRF"), within the tissue's blood vessels. Nitric oxide is a powerful biologic signaling molecule, which acts as a vasodilator relaxing the smooth muscle surrounding arterial blood vessels. The dilation of these arterial blood vessels increases the blood flow in the vessel and, as a result, in the surrounding tissue. Moreover, nitric oxide release is also linked to the formation and growth of new blood vessels in tissue. Accordingly, application of ultrasonic stimuli increases the collateral circulation and perfusion in ischemic tissues. The inventors also believe that increases in temperature associated with ultrasound may further enhance tissue perfusion.

Application of ultrasound with a hand-held transducer is limited due to the narrow field of application, which makes application of ultrasound to an entire extremity difficult and time consuming. Moreover, hand-held transducers are likely ineffective in delivering uniform increase in blood flow to the extremity.

As such, various embodiments of the present invention provide for an ultrasonic bath for using ultrasonic energy to enhance tissue perfusion, to enhance the body's ability to develop collateral blood vessels and/or to enhance collateral circulation in an extremity in need thereof. The ultrasonic bath may comprise a basin configured with one or more ultrasonic transducers to generate and transmit ultrasound energy to an extremity, wherein the basin is adapted to hold media and to permit immersion of an extremity. The ultrasonic bath may further comprise a transducer control unit to control the amplitude, frequency, power and/or duration of ultrasonic energy. The ultrasonic bath may also further comprise an inlet and/or an outlet to fill the basin with media or to drain the basin of the media. In a particular embodiment, the inlet and outlet may be the same element on the ultrasonic bath to serve a dual purpose.

The basin may be made from any appropriate material known in the art. In one embodiment, the basin may be made of stainless steel. The basin may be any suitable size and shape that permits the immersion of an extremity. In various embodiments, the size and shape of the basin may be configured particularly for use with a particular extremity. In one particular embodiment, the basin may be about 20 inches in length, about 12 inches in width and about 40 inches in depth. The basin size of this embodiment may be particularly useful for immersion and treatment of a leg. In another particular embodiment, the basin is adapted to permit the immersion of an entire extremity.

In various embodiments, the ultrasonic transducer may be adapted to generate and transmit ultrasonic energy at a frequency of about 18 kHz to about 3 mHz. In some embodiments the frequency may be about 19 kHz to about 40 kHz. In other embodiments, the ultrasonic transducer may be adapted to generate and transmit a power output of about 0.01 watt per $cm^2$ to about 20.0 watts per $cm^2$. In particular embodiments, the ultrasonic transducer may be adapted to generate and transmit a power output of about 0.25 watt per $cm^2$ to about 5.0 watts per cm². In one particular embodiment, the power output may be about 1 watt per cm². The media placed in the basin allows for uniform transmission of ultrasonic energy from the ultrasonic transducer to the extremity that is immersed in the media and surrounded by the media.

In a further embodiment, the basin may further comprise a heating element to heat media that is placed into the basin. In one embodiment, the ultrasonic transducer may also be used as a heating element by its transfer of ultrasound energy into the media. In another embodiment, the heating element may be a separate element to provide heat to the media.

Additional embodiments of the present invention provide for methods of using ultrasonic energy to enhance tissue perfusion, to enhance the body's ability to develop collateral vessels, and/or to enhance collateral circulation in an extremity in need thereof. The method comprises providing an ultrasonic bath as described herein, placing an extremity in need of treatment into the ultrasonic bath and using the ultrasonic bath to apply ultrasonic energy to the extremity. In one embodiment, the extremity in need of treatment is placed in the inventive ultrasonic bath and ultrasonic energy is applied to the extremity for at least 5 minutes. In another embodiment, the extremity in need of treatment is placed in the inventive ultrasonic bath and ultrasonic energy is applied to the extremity for up to 90 minutes. The use of a lower power level may allow for a longer period of treatment. Thus, in some embodiments, treatment for more than 90 minutes may be performed. In other embodiments, the extremity in need of treatment is placed in the ultrasonic bath and ultrasonic energy is applied to the extremity for about 15, 30, 45, 60, or 75 minutes. One of skill in the art will be able to determine the appropriate period of treatment. In further embodiments, serial treatments for the extremity in need of treatment may be performed to enhance tissue perfusion, to enhance the body's ability to develop collateral vessels, and/or to enhance collateral circulation in an ischemic extremity. For example, the inventive ultrasonic bath may be provided to a patient for home use and the patient may be instructed to use the ultrasonic bath several times a day (e.g., four times a day). In other embodiments, a patient may visit an outpatient facility to receive the treatment using the ultrasonic bath and thus treatment may be one or more times per week (e.g., once per week, three times per week, five time per week). One of skill in the art will be able to determine the length, number, and frequency of treatments that are appropriate for an extremity in need of treatment. Factors to consider may include but are not limited to the subject's age, health, extent of arterial occlusion, degree of the peripheral arterial disease, degree of the ischemia, and energy level of the ultrasonic bath.

In a further embodiment, the method may further comprise the application of heat to the extremity. Examples of appropriate temperatures of heat include but are not limited to from room temperature (e.g., about 20° C.) to a temperature that does not cause a high level of discomfort or burns to the extremity (e.g., about 43° C. to 48° C.). In various embodiments, the temperature may be about 20° C., 25° C., 30° C., 35° C., 40° C., about 45° C. Application of heat may be performed by heating the media in the ultrasonic bath. Heating the media may be performed before placing the extremity in need of treatment into the ultrasonic bath or while the extremity in need to treatment is immersed in the media in the ultrasonic bath. In other embodiments, the application of heat to the extremity may be performed before the extremity receives the ultrasound treatment or after the extremity received the ultrasound treatment.

Example

The following examples are provided to better illustrate the claimed invention and is not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Transcutaneous Application of Ultrasound and Measurement of Transcutaneous Oxygen Tension A transcutaneous oxygen tension monitor was placed on the left extremity and the corresponding right extremity. Measurement of the transcutaneous oxygen tension is a method of evaluating blood flow in settings where tissue viability and the blood flow are of concern. If the transcutaneous oxygen tension is too low, a surgeon may decide to amputate the extremity. Since the transcutaneous oxygen tension displayed by the transcutaneous oxygen tension monitor changes very frequently, a series of measurements was recorded over a short period of time (e.g., 10 seconds, 30 seconds, 1 minute, etc.) and the mean transcutaneous oxygen tension was determined and used as it provides a better indication of the transcutaneous oxygen tension.

The transcutaneous oxygen tension in both the left extremity and the corresponding right extremity were measured prior to immersing the left extremity into the ultrasonic bath. The left extremity was immersed in the apparatus containing water and ultrasound was applied through the water to the extremity for five minutes. The transcutaneous oxygen tension was measured in both the left extremity and the corresponding right extremity after removing the left extremity from the apparatus. Again, a series of measurements was taken and the mean value was used. The right extremity did not receive treatment.

In the treatment group (i.e., left extremities) of 28, 23 showed 7-52% increase in the transcutaneous oxygen tension in the extremity; 2 showed a decrease in the transcutaneous oxygen tension in the extremity; and 1 showed no significant change in the transcutaneous oxygen tension in the extremity. In the non-treatment group (i.e., right extremities) of 23, 14 showed a 5-70% increase of transcutaneous oxygen tension in the extremity; 5 showed a decrease in the transcutaneous oxygen tension in the extremity; and 4 showed no significant change in the transcutaneous oxygen tension in the extremity. Although the corresponding right extremity was not treated, treatment in the left extremity was able to affect the blood vessels of the corresponding untreated extremity. The details of the tests are summarized in tables 1 and 2.

TABLE 1

| | Upper Extremities | | | | | | | | | | | |
|---|---|---|---|---|---|---|---|---|---|---|---|---|
| | L. arm pre USD | Post USD | L. palm pre USD | Post USD | L. index pre USD | Post USD | R. arm pre USD | Post USD | R. palm pre USD | Post USD | R. index pre USD | Post USD |
| Case 1 | 39 | 84 | 115 | 153 | 52 | 163 | 23 | 60 | 71 | 111 | 74 | 37 |
| | 31 | 74 | 112 | 103 | 55 | 118 | 25 | 58 | 66 | 119 | 59 | 35 |
| | 33 | 92 | 109 | 83 | 50 | 78 | 38 | 57 | 99 | 120 | 56 | 34 |
| | 40 | 67 | 107 | 75 | 43 | 66 | 44 | 59 | 91 | 114 | 55 | 33 |
| | 45 | 63 | 106 | 69 | 40 | 63 | | 59 | 85 | 117 | | 33 |
| | 50 | 64 | 103 | 64 | 36 | 60 | | 63 | 84 | 114 | | 32 |
| | 49 | 50 | 101 | 69 | 36 | 81 | | 58 | | | | 35 |
| | 57 | | 96 | | 37 | | | | | | | |
| | 55 | | 91 | | 36 | | | | | | | |
| Mean | 44.3 | 70.6 incre 37% | 104.4 | 88.0 | 42.8 | 89.9 incre 52% | 32.5 | 59.1 incre 45% | 82.7 | 115.8 incre 29% | 61.0 | 34.1 |
| Case 2 | 14 | 32 | 77 | 99 | 75 | 77 | 8 | 50 | 74 | 77 | 88 | 52 |
| | 32 | 25 | 78 | 92 | 62 | 70 | 9 | 50 | 71 | 76 | 74 | 51 |
| | 21 | 30 | 77 | 88 | 57 | 67 | 15 | 52 | 73 | 77 | 69 | 51 |
| | 22 | 40 | 65 | 85 | 55 | 63 | 12 | 49 | 75 | 76 | 65 | 49 |
| | 26 | 46 | 58 | 82 | 51 | 59 | 18 | 54 | 75 | 76 | 62 | 48 |
| | 32 | 50 | 56 | 78 | 49 | 57 | 21 | 59 | 76 | 75 | 58 | 48 |
| | 37 | 50 | 58 | 77 | 46 | 54 | 29 | 63 | 79 | 74 | 55 | 47 |
| | 40 | 56 | | | | | | | | | | |
| Mean | 28.0 | 41.1 incre 32% | 67.0 | 85.9 incre 22% | 56.4 | 63.9 incre 12% | 16.0 | 53.9 incre 70% | 74.7 | 75.9 | 67.3 | 49.4 |
| Case 3 | 38 | 64 | 150 | 156 | 82 | 94 | 95 | 95 | 153 | 149 | | |
| | 35 | 44 | 150 | 153 | 70 | 86 | 84 | 99 | 153 | 149 | | |
| | 42 | 45 | 150 | 152 | 67 | 79 | 90 | 100 | 153 | 149 | | |
| | 44 | 50 | 142 | 151 | 64 | 72 | 96 | 114 | 137 | 149 | | |
| | 49 | 53 | 150 | 150 | 62 | | 97 | 90 | 132 | 151 | | |
| | 54 | 55 | 150 | 149 | 59 | | | 88 | 128 | 151 | | |
| | 56 | | 150 | | 54 | | | | | | | |
| | 59 | | | | 52 | | | | | | | |
| | 56 | | | | | | | | | | | |
| Mean | 48.1 | 51.8 incre 7% | 148.9 | 151.8 | 63.8 | 82.8 incre 23% | 92.4 | 97.7 incre 5% | 142.7 | 149.7 incre 5% | | |

TABLE 2

| | Lower Extremities | | | | | | | | | | | |
|---|---|---|---|---|---|---|---|---|---|---|---|---|
| | R. knee pre USD | Post USD | R. ankle pre USD | Post USD | R. foot pre USD | Post USD | L. knee pre USD | Post USD | L. ankle pre USD | Post USD | L. foot pre USD | Post USD |
| Case 4 | 33 | 73 | 73 | 58 | 11 | 70 | 13 | 15 | 46 | 68 | 44 | 68 |
| | 38 | 75 | 66 | 56 | 33 | 65 | 38 | | 61 | 51 | 47 | 46 |
| | 53 | 75 | 67 | 56 | 40 | 66 | 39 | | 66 | 67 | 44 | 40 |
| | 53 | 74 | 57 | 59 | 35 | 67 | 38 | | | 27 | | 37 |
| | 50 | 73 | 51 | 55 | 37 | 64 | | | | | | 36 |
| | 55 | 71 | 52 | 53 | 42 | 63 | | | | | | 38 |
| | | 70 | | | | | | | | | | 41 |
| | | | | | | | | | | | | 42 |
| Mean | 47.0 | 73.0 incre 35% | 61.0 | 56.2 | 33.0 | 65.8 incre 50% | 32.0 | 15.0 | 57.7 | 53.3 | 45.0 | 43.5 |
| Case 5 | | | 46 | 66 | 51 | 55 | 57 | 62 | 74 | 60 | 40 | 85 |
| | | | 42 | 68 | 55 | 53 | 47 | 54 | 40 | 65 | 48 | 30 |
| | | | 53 | 71 | 48 | 55 | 59 | 60 | 51 | 67 | 53 | 52 |
| | | | 53 | 73 | 47 | 55 | 65 | 63 | 57 | 71 | | 48 |
| | | | 57 | 74 | 54 | 56 | | 66 | | 71 | | 47 |
| | | | 63 | 72 | 51 | 54 | | 65 | | | | 57 |
| | | | 52.3 | 70.7 incre 26% | 51.0 | 54.7 incre 7% | 57.0 | 61.7 incre 7% | 55.5 | 66.8 incre 17% | 47.0 | 53.2 incre 11% |
| Case 6 | 99 | 39 | 64 | 31 | 21 | 27 | | | 91 | 55 | 31 | 39 |
| | 92 | 41 | 47 | 30 | 32 | 42 | | | 81 | 59 | 36 | 38 |
| | | 45 | | 39 | 29 | 34 | 45 | | 72 | 61 | 30 | 38 |
| | | | | 28 | 29 | 31 | 46 | | | 62 | 39 | 37 |
| | | | | | | 47 | | | | 63 | 37 | 37 |
| | | | | | | | | | | | 38 | |
| Mean | 95.5 | 41.7 | 44.5 | 29.8 | 29.5 | 41.4 incre 29% | | | 81.3 | 60.0 | 35.2 | 37.8 |

TABLE 2-continued

Lower Extremities

|  | R. knee pre USD | Post USD | R. ankle pre USD | Post USD | R. foot pre USD | Post USD | L. knee pre USD | Post USD | L. ankle pre USD | Post USD | L. foot pre USD | Post USD |
|---|---|---|---|---|---|---|---|---|---|---|---|---|
| Case 7 | 16 | 54 | 26 | 42 | 33 | 36 | 88 | 58 | 45 | 58 | 27 | 69 |
|  | 18 | 58 | 44 | 46 | 43 | 46 | 19 | 56 | 37 | 61 | 37 | 78 |
|  | 39 | 62 | 43 | 41 | 35 | 52 | 31 | 56 | 54 | 61 | 24 | 79 |
|  | 40 | 64 | 34 | 41 | 32 | 53 | 39 | 58 | 57 | 64 | 25 | 79 |
|  | 40 | 66 | 27 | 36 |  | 53 | 50 | 57 | 46 | 64 | 26 | 81 |
|  | 47 | 68 |  | 36 |  | 51 | 57 | 55 | 46 | 64 | 56 | 77 |
|  |  | 67 |  |  |  |  |  | 58 | 49 | 66 |  |  |
| Mean | 33.3 | 62.7 | 34.8 | 40.3 | 35.8 | 48.5 | 47.3 | 56.9 | 47.7 | 62.6 | 32.5 | 77.2 |
|  |  | incre 47% |  | incre 14% |  | incre 26% |  | incre 17% |  | incre 24% |  | incre 58% |
| Case 8 | 39 | 71 | 67 | 67 | 64 | 84 | 45 | 70 | 42 | 78 | 57 | 67 |
|  | 57 | 67 | 60 | 68 | 60 | 70 | 46 | 67 | 66 | 74 | 61 | 68 |
|  | 62 | 72 | 57 | 65 | 57 | 66 | 45 | 53 | 70 | 74 | 64 | 65 |
|  | 64 | 69 | 58 | 63 | 54 | 63 | 44 | 88 | 69 | 75 | 64 | 65 |
|  | 64 | 72 | 58 | 64 | 53 | 61 | 46 | 64 | 67 | 74 | 63 | 65 |
|  | 67 | 73 | 58 | 65 | 52 | 59 | 50 | 68 | 88 | 75 | 63 | 66 |
|  |  | 77 |  |  |  | 59 | 52 | 74 | 72 | 79 |  | 66 |
| Mean | 58.8 | 71.6 | 59.7 | 65.3 | 56.7 | 66.0 | 46.9 | 69.1 | 67.7 | 75.6 | 62.0 | 66.0 |
|  |  | incre 18% |  | incre 8% |  | incre 14% |  | incre 32% |  | incre 10% |  | incre 6% |
| Case 9 | 34 | 53 | 29 | 47 |  |  |  |  | 43 | 53 | 42 | 55 |
|  | 44 | 59 | 31 | 42 |  |  |  |  | 48 | 54 | 55 | 56 |
|  | 48 | 60 | 31 | 38 |  |  |  |  | 51 | 53 | 60 | 54 |
|  | 51 | 61 | 32 | 34 |  |  |  |  | 51 | 52 | 61 | 53 |
|  | 52 | 61 | 30 | 31 |  |  |  |  | 51 | 51 | 60 | 51 |
| Mean | 45.8 | 58.8 | 30.6 | 38.4 |  |  |  |  | 48.8 | 52.6 | 55.6 | 53.8 |
|  |  | incre 22% |  | incre 20% |  |  |  |  |  | incre 7% |  |  |
| Case 10 | 65 | 74 | 63 | 58 | 47 | 25 |  |  |  |  |  |  |
|  | 68 | 71 | 56 | 60 | 15 | 36 |  |  |  |  |  |  |
|  | 68 | 76 | 52 | 51 | 24 | 45 |  |  |  |  |  |  |
| Mean | 67.0 | 73.7 | 57.0 | 53.0 | 28.7 | 35.3 |  |  |  |  |  |  |
|  |  | incre 9% |  |  |  | incre 19% |  |  |  |  |  |  |

Example 2

Figures 1, 2:
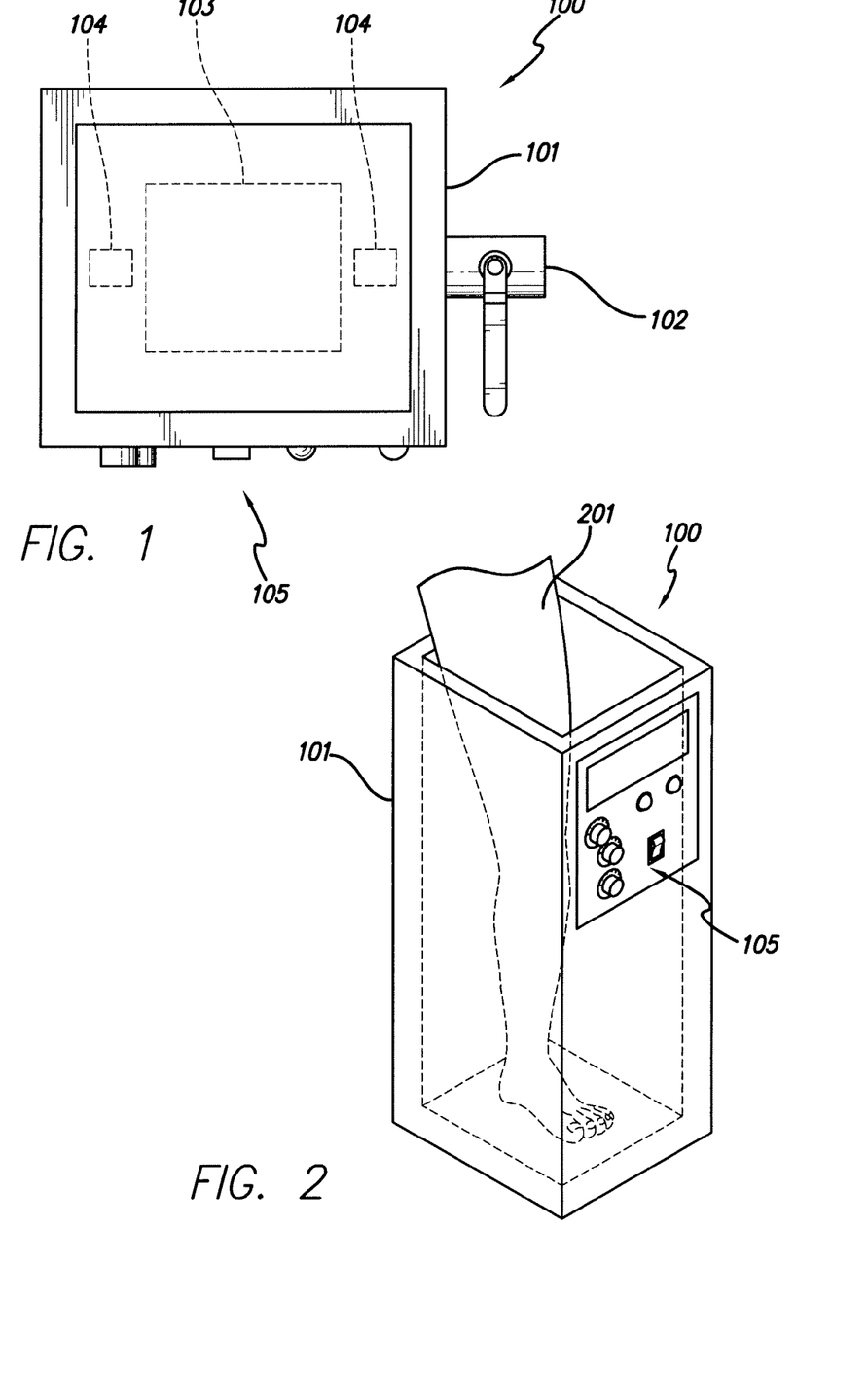
FIG. 1 depicts a basin of an ultrasonic bath in accordance with an embodiment of the present invention.
FIG. 2 depicts an ultrasonic bath with a subject's leg immersed in the basin in accordance with an embodiment of the present invention.

In accordance with one embodiment of the invention, FIG. 1 depicts a top view of one embodiment of the ultrasonic bath 100. As shown, the ultrasonic bath comprises a basin 101, an outlet 102, an ultrasound transducer 103 that is underneath the basin 101, heating elements 104 that are also underneath the basin 101, and a transducer control unit 105.

In accordance with another embodiment of the invention, FIG. 2 depicts a subject's leg 201 placed in the ultrasonic bath 100. The basin 101 and a transducer control unit 105 are also shown.

Figure 3:
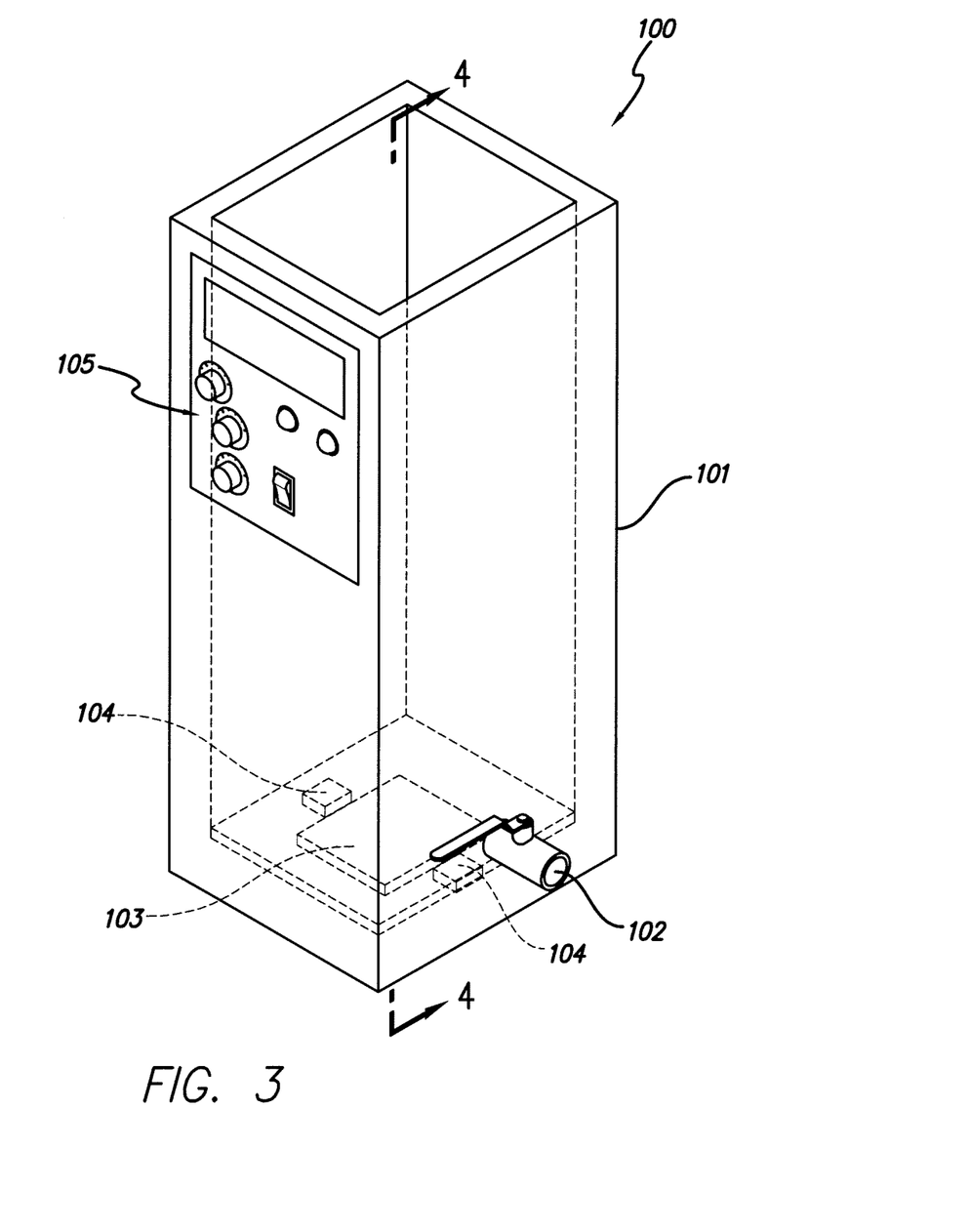
FIG. 3 depicts an exterior view of an ultrasonic bath in accordance with an embodiment of the present invention.

In accordance with another embodiment of the invention, FIG. 3 depicts an exterior view of an ultrasonic bath 100. An outlet 102 is used to drain the basin after use. A transducer control unit 105 is used to control the amplitude, frequency, power and/or duration of ultrasonic energy. Also shown is the transducer 103 underneath the basin 101, as well as heating elements 104 being underneath the basin 101.

Figure 4:
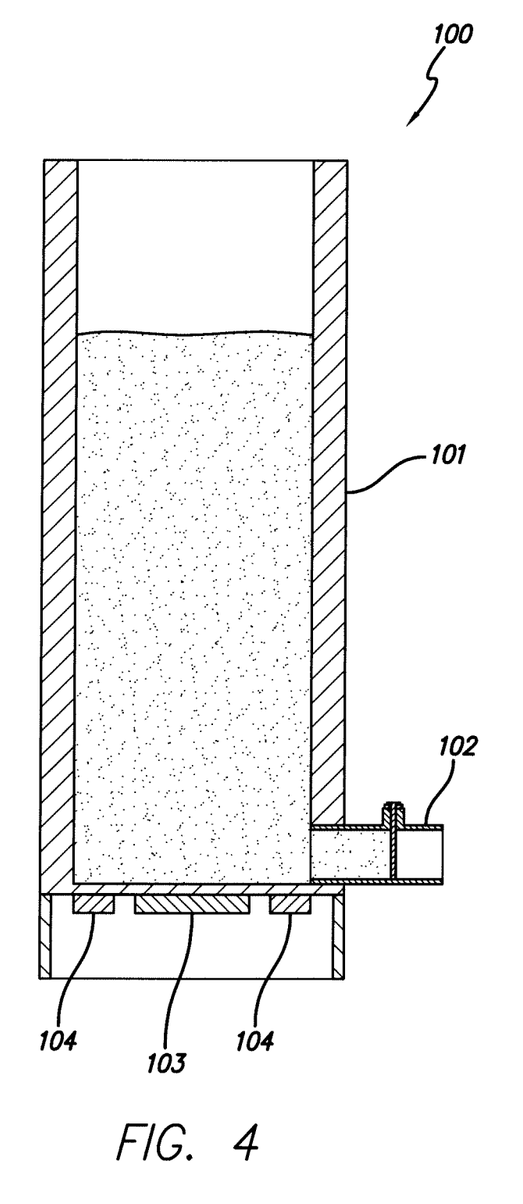
FIG. 4 depicts a partial view ultrasonic bath with an ultrasonic transducer underneath the basin in accordance with an embodiment of the present invention.

In accordance with another embodiment of the invention, FIG. 4 depicts a representation of an ultrasonic bath 101, with an ultrasonic transducer 103 underneath the basin 101. The outlet 102 allows for drainage of the basin. Heating elements 104 are also underneath the basin.

In another embodiment, additional ultrasonic transducers 103 are placed underneath the basin 101 (not shown). In an alternative embodiment, one or more transducers 103 are place on the side of the basin (not shown). Alternatively, one or more transducers 103 are immersed in the basin 101 (not shown).

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method for enhancing the oxygen level in an ischemic extremity, comprising:
   providing a subject having an ischemic extremity;
   providing an ultrasonic bath comprising a basin shaped and sized to hold media and to permit the immersion of an extremity, and one or more ultrasonic transducers to generate and transmit ultrasonic energy to the extremity;
   placing the ischemic extremity in the ultrasonic bath; and
   using the ultrasonic bath to apply ultrasonic energy from the ultrasonic transducer to the ischemic extremity, thereby enhancing the oxygen level in the ischemic extremity.

2. The method of claim 1, further comprising applying heat to the extremity.

3. The method of claim 1, wherein the extremity is selected from the group consisting of an arm, hand, finger, leg, foot, toe and combinations thereof.

4. The method of claim 1, wherein the basin is about 20 inches in length, about 12 inches in width and about 40 inches in depth.

5. The method of claim 1, wherein the media comprises a saltwater solution having a salt concentration of between 0.25% and 10%.

6. The method of claim 1, wherein the ultrasonic bath further comprises a heating element.

7. The method of claim 1, wherein the ultrasonic energy is at a frequency of about 18 kHz to about 3 MHz.

8. The method of claim 1, wherein the ultrasonic energy is at a power level of about 0.01 watt per $cm^2$ to about 20.0 watts per $cm^2$.

9. The method of claim 1, wherein the ultrasonic energy is at a power level of about 0.25 watt per $cm^2$ to about 5.0 watts per $cm^2$.

10. The method of claim 1, wherein using the ultrasonic bath comprises applying ultrasonic energy for at least five minutes.

11. The method of claim 1, wherein using the ultrasonic bath comprises applying the ultrasonic energy for less than or equal to 90 minutes.

12. The method of claim 1, wherein using the ultrasonic bath comprises serial treatments for the extremity.

* * * * *